US00PP32752P2

(12) United States Plant Patent
Hansen

(10) Patent No.: US PP32,752 P2
(45) Date of Patent: Jan. 12, 2021

(54) ***BRUNNERA MACROPHYLLA* PLANT NAMED 'JACK OF DIAMONDS'**

(50) Latin Name: ***Brunnera macrophylla* (Adams) I. M. Johnston**
Varietal Denomination: Jack of Diamonds

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/602,166

(22) Filed: Aug. 20, 2019

(51) Int. Cl.
*A01H 5/02* (2018.01)
*A01H 6/00* (2018.01)

(52) U.S. Cl.
USPC ..... Plt./412

(58) Field of Classification Search
USPC ..... Plt./412
See application file for complete search history.

*Primary Examiner* — Susan McCormick Ewoldt

(57) ABSTRACT

The new and distinctive cultivar of *Brunnera* plant named 'Jack of Diamonds' with very large leaves of silver with broad, dark green around the veins. The flowers are light blue and flower for about four weeks in the spring. The leaves are thicker and provide more tolerance of high temperatures and other environmental factors.

2 Drawing Sheets

Botanical classification: *Brunnera macrophylla* (Adams) I. M. Johnston.

Variety denomination: 'Jack of Diamonds'.

STATEMENT REGARDING PRIOR DISCLOSURES UNDER 37 CFR 1.77(B)(6)

The first public disclosure of the claimed plant was a private sale to Corso's Flower and Garden Center by Walters Gardens, Inc. on Sep. 4, 2018. The claimed plant was disclosed on Dec. 1, 2018 as a non-enabling photograph and brief description on a website operated by Walters Gardens, Inc., who obtained the plant and all information relating thereto, from the inventor. No plants of *Brunnera* 'Jack of Diamonds' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

*Brunnera macrophylla* is a hardy, herbaceous, sub-alpine perennial native to eastern Asia, western Caucasus and Mediterranean Europe. It has many common names, among them: Heartleaf *Brunnera*, Siberian Bugloss, and Perennial Forget-me-not.

The new and distinct *Brunnera macrophylla* 'Jack of Diamonds', hereinafter also referred solely by the cultivar name 'Jack of Diamonds' and "the new plant," is a new and unique seedling hybridized by the inventor on May 15, 2015 between 'Caucasian Carpet' (not patented) times 'Jack Frost' U.S. Plant Pat. No. 13,859. The new plant passed initial evaluation in the fall of 2016 and was assigned the breeder code 15-4-10 through the remaining evaluation process until given a cultivar name. 'Jack of Diamonds' has been asexually propagated by sterile tissue culture propagation of the shoot tips, at the same nursery in Zeeland, Mich. since fall of 2016. The asexually produced plants are identical to the originally plant, and maintains those unique characteristics in subsequent generations.

BRIEF DESCRIPTION OF THE PLANT

*Brunnera macrophylla* 'Jack of Diamonds' is distinct from all other Heartleaf *Brunnera* known to the inventor. The most closely comparison cultivars are listed below. 'Jack Frost' U.S. Plant Pat. No. 13,859, the male parent has similar leaf coloration, but the foliage is smaller in size. The female parent, 'Caucasian Carpet', has a shorter habit that is more stoloniferous with smaller solid-green leaves. 'Looking Glass' U.S. Plant Pat. No. 17,829 has more silver covering the leaf, smaller leaf blades and the quality is lower and the plant heat tolerance is less. 'Sea Heart' U.S. Plant Pat. No. 24,684 has leaf blades that are not as large. 'Silver Heart' U.S. Plant Pat. No. 24,685 has narrower green surrounding the veins and move silver, and the foliage is not as large. 'Sterling Silver' U.S. Plant Pat. No. 31,280 has smaller leaves and more silvering in the leaf. Copending 'Queen of Hearts' has narrower green surrounding the leaf veins and more silver to the leaf blades. 'Alexander's Great' U.S. Plant Pat. No. 25,789 has flatter foliage with narrower green surrounding the veins. The silver color of the foliage of 'Alexander's Great' is more muted and less concentrated than the new plant, and the green surrounding the leaf veins is darker on the new plant. The leaves of 'Jack of Diamonds' are thicker than 'Jack Frost', 'Looking Glass' and 'Alexander's Great'.

*Brunnera* 'Jack of Diamonds' differs from all other Heartleaf *Brunnera* in the following repeatedly observed trait combination:

1. Large plants of rounded-mounds, clumping, winter-hardy, perennial habit;
2. Foliage without a stem, held up on stiff petioles;
3. Very large, heart-shaped leaf blade color is silver between the veins with moderate width dark green surrounding the veins;
4. Numerous flowers on tall stems;

5. Leaves are thick and cordate-shaped with bases frequently overlapping;
6. Plant is tolerant of high temperatures.

BRIEF DESCRIPTION OF THE DRAWINGS

The photographs of the new invention demonstrate the overall appearance, including the unique traits, of plants growing in a partially shaded trial garden in Zeeland, Mich. The colors are as accurate as reasonably possible with color reproductions. Variation in ambient light spectrum, source and direction may cause the appearance of slight variation in brightness, saturation and hue.

DETAILED DESCRIPTION OF THE PLANT

Figure 1:
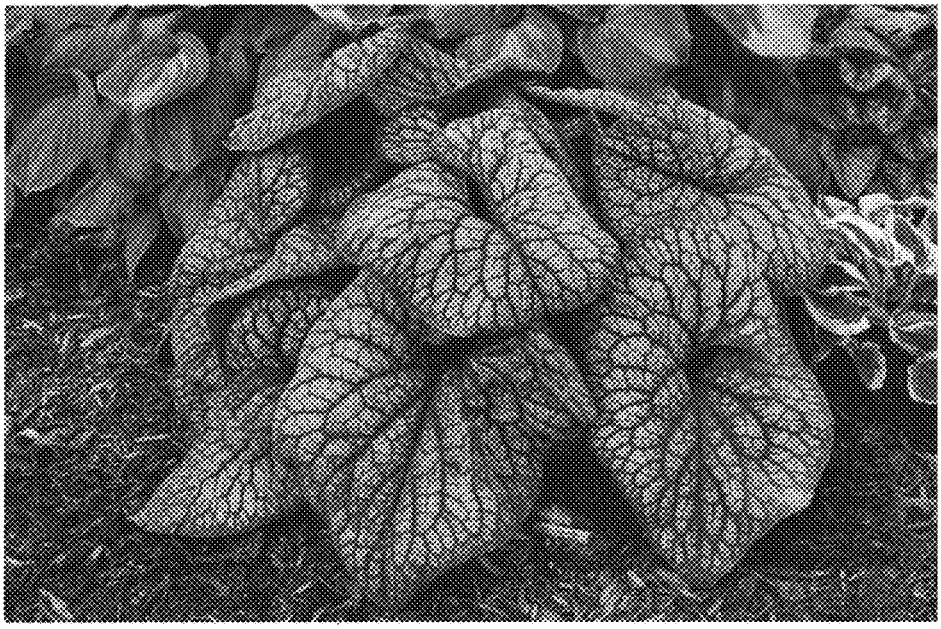
FIG. 1 shows a close-up of a leaf of a two-year-old plant in early summer foliage.
Figure 2:
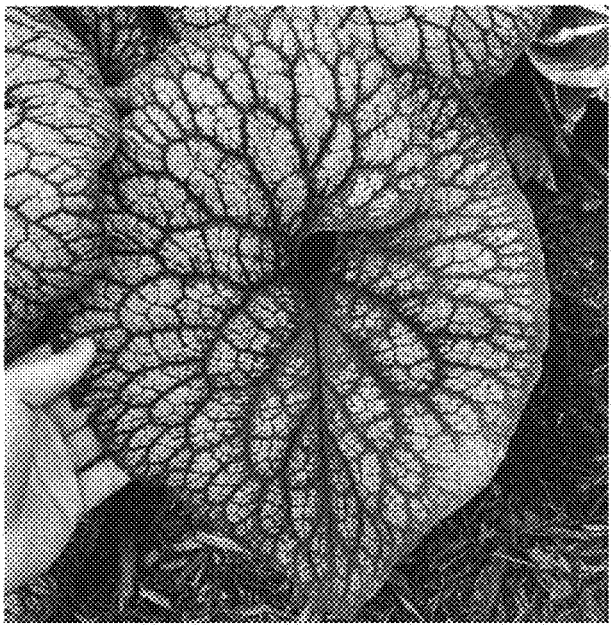
FIG. 2 shows a close-up of a leaf from a two-year-old plant in early summer foliage.
Figure 3:
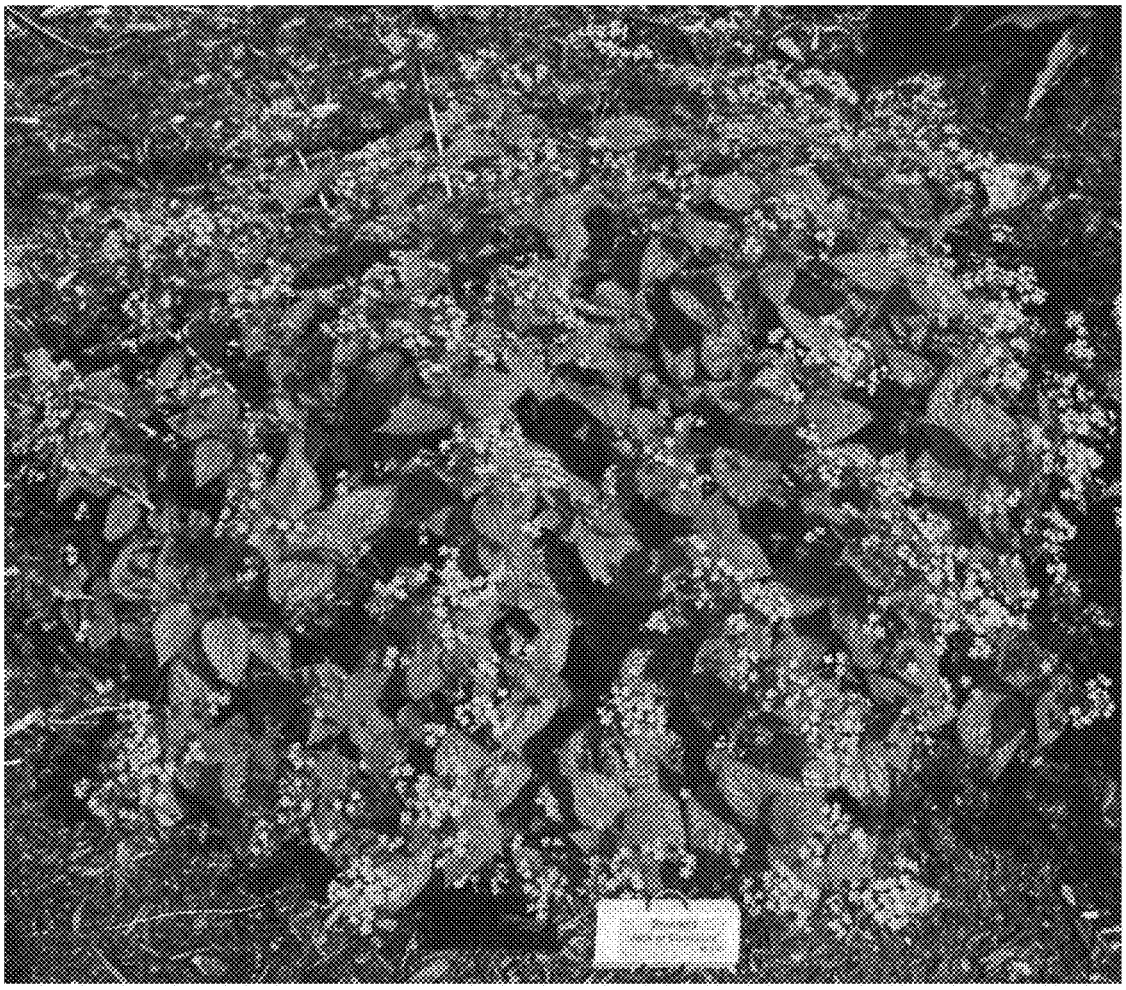
FIG. 3 shows a three-year-old new plant in full flower in the spring.

The following descriptions with generic dictionary color usage are of a three-year-old plant growing in Zeeland, Mich. For more precise color descriptions the 2015 edition of The Royal Horticultural Colour Chart and the corresponding color references are used. The new plant has not been evaluated in all possible growing environments. The phenotype may vary slightly with different conditions such as fertility, light, moisture and temperature, however the genotype remains stable.

Plant habit: Winter-hardy, mounded, domed-shaped, herbaceous perennial of acaulescent foliage and with panicles in spring; foliage to 48.0 cm tall and 84.0 cm wide.

Leaves: Reniform to cordate; apex broadly acute; base cordate with lobes frequently imbricate; margin ciliolate; blade flat without undulations; adaxial and abaxial hirsutulous; acaulescent leaves about 16.0 cm to 30.0 cm long and 15.0 to 30.0 cm in width; average 26.5 cm long and 26.0 cm wide; cauline leaves average about 5.5 cm wide and 6.0 cm long, decreasing in size distally; about six acaulescent leaves per shoot and five cauline leaves per stem;

Leaf color: Acaulescent leaves — adaxial surface nearest RHS 137A to about 2.0 mm to 6.0 mm surrounding major veins and the margin 5.0 mm of leaf, silver portion between veins lighter than RHS 192D or RHS 190D; abaxial surface between RHS 146B and 146C; cauline leaves — adaxial surface nearest RHS 146D with patches of variable sizes between veins of nearest RHS 192D or RHS 190D; abaxial surface nearest RHS 146B.

Petioles: Concavo-convex; hirsutulous, to 9.0 mm wide at base and up to 30 cm long; distally nearest RHS 146D and proximally nearest RHS N77D;

Venation: Reticulate; impressed and glabrous adaxial, costate and hirsutulous abaxial;

Vein color: Adaxial main and secondary nearest RHS 146C, abaxial nearest RHS 146D;

Inflorescence: Branched paniculate cyme with cauline leaves; about 240 flowers; to about 66.0 cm long and flowering in the upper 39.0 cm about 24.0 cm wide, about 5.0 mm at base;

Flower buds about one to two days prior to opening: Ellipsoidal; rounded apex and slightly attenuate base; to about 3.0 mm long and 2.0 mm diameter near apex;

Flower bud color: One day prior to opening — exposed petals nearest RHS 92D with petal margins intensified to nearest RHS 92B; sepals nearest RHS 143D; about three days prior to opening — exposed petals between RHS 75D and RHS 75D;

Flower lasting: Inflorescence remaining in effective flower for about four weeks, individual flowers persist up to one week;

Flower timing: Beginning late April and continuing for about four weeks;

Flower: Perfect; complete; actinomophic; rotate; forming five lobed corolla with center corona; about 7.0 mm diameter and corona eye about 2.0 mm tall and 1.5 mm across;

Petals: Typically five; rounded apex, truncate fused base; margin entire; to about 3.0 mm long and 2.0 mm wide;

Petal color: Adaxial mature face nearest RHS 104B with corona nearest RHS 158A, abaxial nearest 108 D; adaxial young face between RHS 104B and RHS 104A with corona nearest NN155D, abaxial nearest RHS 100C;

Sepals: Five; forming campanulate calyx; lanceolate; narrowly acute apex; fused in basal 0.7 mm; entire margin; about 1.5 mm long and about 0.5 mm across;

Sepal color: Nearest RHS 138B;

Peduncles: Cylindrical; pubescent to hirsutulous; erect; with cauline leaves; to about 66.0 cm long and about 5.0 mm diameter;

Peduncle color: Nearest RHS 138B with undertone of nearest RHS 77A or RHS 187A;

Peduncle branches: Micro-hirsutulous; cylindrical; to about 12.5 cm long and 1.0 mm diameter;

Peduncle branches color: Nearest RHS 146A;

Pedicels: Cylindrical; finely puberulent; mostly upright; to about 5.0 mm long and 1.0 mm diameter;

Pedicel color: Nearest RHS 138B with undertone of nearest RHS 187A;

Androecium: Five; fused to inner corona;

*Filaments*.—Cylindrical; about 1.0 mm long; color nearest RHS NN155D.

*Anther*.—Ellipsoidal: about 1.0 mm long and 0.5 mm diameter; basifixed; color nearest RHS 155A.

*Pollen*.—Nearest RHS 155A.

Gynoecium: One; about 1.2 mm long;

*Style*.—Short, cylindrical; about 0.5 mm long; color nearest RHS 145C.

*Stigma*.—Globose; about 0.2 mm diameter; color nearest RHS 145C.

Seeds: Small nutlet; enclosed within calyx; one to four per flower; about 0.5 mm diameter; color nearest RHS 202A;

'Jack of Diamonds' is winter-hardy to USDA zone 3, tolerates late spring frosts, and persists after fall frosts. 'Jack of Diamonds' performs best in light shade, with ample moisture, and good drainage. It is also well suited for growing in the landscape as a specimen plant, en mass, or in containers. 'Jack of Diamonds' is less prone to leaf scorch than 'Variegata' (not patented) and is more tolerant of high temperatures than 'Looking Glass'. The new plant has shown no other susceptibility or tolerance to pests and diseases except that which is common to *Brunnera*.

I claim:

1. A new and distinct perennial Heartleaf *Brunnera* plant named 'Jack of Diamonds' as herein described and illustrated.

* * * * *